United States Patent [19]

Swindell

[11] Patent Number: 4,758,569
[45] Date of Patent: Jul. 19, 1988

[54] DOXAZOSIN AS AN ANTI-ATHEROSCLEROSIS AGENT

[75] Inventor: Archie C. Swindell, Groton, Conn.

[73] Assignee: Pfizer Inc., New York, N.Y.

[21] Appl. No.: 89,716

[22] Filed: Aug. 26, 1987

[51] Int. Cl.$^4$ .............................................. A61K 31/50
[52] U.S. Cl. ...................................... 514/254; 514/824
[58] Field of Search ........................ 514/222, 824, 254

[56] References Cited

U.S. PATENT DOCUMENTS

| | | | |
|---|---|---|---|
| 4,130,647 | 12/1978 | Taylor | 424/251 |
| 4,188,390 | 2/1980 | Campbell | 424/251 |
| 4,361,564 | 11/1982 | Edwards | 424/250 |
| 4,532,135 | 7/1985 | Edwards | 514/222 |
| 4,582,832 | 4/1986 | Swindell | 514/254 |

OTHER PUBLICATIONS

Swindell, A. C. et al., Effects of Doxazosin on Diet-Induced Hypercholesterolemia in C57BR/cdJ Mice, Am. J. Cardiology 59: 29G–34G, 1987.

Woodside, W. F. et al., Effects of $\alpha_1$-Inhibition on Lipid Metabolism in the Rat. J. Cardiovascular Pharmacology 10 (Suppl. 9): S-27–S34, 1987.

Primary Examiner—Allen J. Robinson
Attorney, Agent, or Firm—Peter C. Richardson; Albert E. Frost; Gregg C. Benson

[57] ABSTRACT

This invention relates to the use of doxazosin or a pharmaceutically acceptable acid addition salt thereof as an agent for retarding the development of atherosclerosis in a mammal, especially for reducing atherosclerotic plaque involvement and for retarding and reducing both the fibrosis and lipid deposition of developing atherosclerotic plaques associated with atherosclerosis.

6 Claims, No Drawings

DOXAZOSIN AS AN ANTI-ATHEROSCLEROSIS AGENT

BACKGROUND OF THE INVENTION

1. Field of the Invention

This invention relates to the use of doxazosin or a pharmaceutically acceptable acid addition salt thereof for retarding the development of arterial disease in mammals. More specifically, it relates to a method for suppressing fibrosis and lipid deposition of developing atherosclerotic plaques and reducing atherosclerotic plaque involvement in mammals having atherosclerosis by administering to said mammals doxazosin or a pharmaceutically acceptable acid addition salt thereof.

2. General Background

Atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" (plaques) in the carotid, coronary and cerebral arteries and in the aorta. These, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Statistical evidence suggests that hyperlipidemia and hypertension are primary risk factors in causing atherosclerosis. Treatment of atherosclerosis is, therefore, approached by attempts to control hypertension and hyperlipidemia by dietary or pharmacological means. Some success has been achieved in reducing the incidence and severity of atherosclerosis by strict adherence to a prudent diet, by lowering plasma lipids with drugs or with ileal bypass surgery and by lowering systemic blood pressure with diet or drugs. However, coronary heart disease remains a threat, even to individuals striving to control their risk factors. It has been speculated that every individual in the United States has some degree of atherosclerosis. This fact, along with the high associated mortality and the inadequacy of the present treatment methods, establishes the need for anti-atherosclerotic agents.

Doxazosin, 4-amino-2-[4-(1,4-benzodioxan-2-carbonyl)piperazin-1-yl]-6,7-dimethoxyquinazoline, its pharmaceutically acceptable acid addition salts and their use as regulators of the cardiovascular system, particularly in the treatment of hypertension are described in U.S. Pat. No. 4,188,390.

The use of trimazosin, 2-hydroxy-2-methylpropyl-4-(4-amino-6,7,8-trimethoxy-2-quinazolinyl)-1-piperazinecarboxylate, or a pharmaceutically acceptable acid addition salt thereof as an agent for retarding the development of atherosclerosis by suppressing fibrosis of atherosclerotic lesions is disclosed and claimed in U.S. Pat. No. 4,582,832.

Prazosin, 1-(4-amino-6,7-dimethoxy-2-quinazolinyl)-4-(2-furanylcarbonyl)piperazine, and its pharmaceutically acceptable acid addition salts as well as trimazosin and its pharmaceutically acceptable acid addition salts, are disclosed in U.S. Pat. No. 4,130,647 as antihypertensive agents useful in treating congestive heart failure and ischemic heart disease.

The use of prazosin among other vasodilators in the prevention of renal failure and damage is disclosed in U.S. Pat. No. 4,361,564. Further, U.S. Pat. No. 4,532,135 discloses the use of trimazosin, doxazosin and prazosin among other vasodilators in preventing renal failure through reduction of plasma lipid levels, a risk factor in renal failure.

However, in spite of the above-mentioned uses for doxazosin and its salts, the use of trimazosin and prazosin as antihypertensive agents and as agents for prevention of renal failure and the use of trimazosin as an anti-atherosclerotic agent, there was, prior to the time of the present invention, no report of the use or intent to use doxazosin or its salts for retarding the development of atherosclerosis, nor any appreciation of its role, or that of its pharmaceutically acceptable acid addition salts in achieving said desirable goal.

SUMMARY OF THE INVENTION

It has now been found that doxazosin or a pharmaceutically acceptable acid addition salt thereof, when administered to a mammal having an atherosclerotic condition, produces a direct therapeutic benefit in retarding the further development of atherosclerosis in said mammal. More specifically, doxazosin, or one of its said salts, when administered in an atherosclerotic treating amount to a mammal having atherosclerosis, reduces aortic atherosclerotic plaque involvement and suppresses fibrosis and lipid deposition in formation of fibrotic lesions or plaque.

The high incidence of atherosclerosis in the United States, noted above, gives rise to normotensive individuals, free of congestive heart disease and/or ischemic heart disease, problems normally considered as cardiac complications of hypertension. The direct therapeutic benefit of doxazosin and its above-mentioned acid addition salts in retarding the development of arterial disease in such individuals occurs at clinically relevant levels of the drug.

DETAILED DESCRIPTION OF THE INVENTION

Doxazosin, which has the chemical structure:

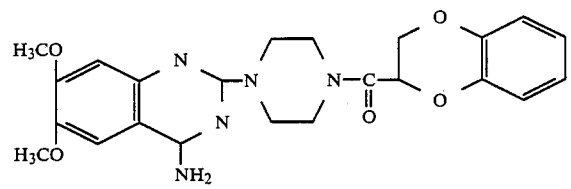

and its pharmaceutically acceptable acid addition salts are described in U.S. Pat. No. 4,188,390.

Although the generic name of doxazosin represents the free base, the present invention is also meant to embrace the pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methane sulfate, ethane sulfate, benzenesulfonate and p-toluenesulfonate salts.

In the treatment of atherosclerosis, doxazosin can be administered via the oral or the parenteral, including transdermal, routes. However, it is generally preferred to administer doxazosin or its pharmaceutically acceptable acid addition salts orally. In general, these compounds are most desirably administered in doses ranging from about 1 mg up to about 32 mg per day, although variations will still necessarily occur depending upon the weight of the subject being treated. The appropriate dose for teatment of atherosclerosis with doxazosin or its pharmaceutically acceptable salts will be readily determined by those skilled in the art of prescribing and/or administering such compounds. However, effective antihypertensive results are achieved with a dosage level that is in the range of from about 0.02 mg to about 0.60 mg/kg of body weight per day, with a preferred maximal oral range in man, being about 0.15 to 0.30 mg/kg per day. Nevertheless, it is still to be appreciated that other variations may also occur in this respect, depending upon the species of mammal being treated and its individual response to said medicament, as well as on the particular type of pharmaceutical formulation chosen in the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include by way of example and not of limitation lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

Although the preferred mode of administration of doxazosin or one of its pharmaceutically acceptable acid addition salts is oral, they may be administered parenterally as well.

For purposes of parenteral administration, solutions of these particular compounds in sesame or peanut oil or in aqueous propylene glycol may be employed, as well as sterile aqueous solutions of the corresponding water soluble acid addition salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. Needless to say, the necessary steps should be taken throughout the preparation of these injectable solutions to insure that the final products are obtained in a sterile condition.

Doxazosin or its pharmaceutically acceptable acid addition salts can also be administered transdermally. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in pending U.S. patent application Ser. No. 925,641 which is assigned to the assignee of this invention, the teachings of which are incorporated herein by reference.

Various procedures and diets have been tested in the rabbit and other animal species in an effort to identify a convenient and accurate model for human atherosclerosis. Initially, diets with added cholesterol were fed to rabbits, and fatty infiltration of their aortas and other arteries were noted. These lesions were composed of lipid filled "foam" cells. They are now known to resemble both morphologically and biochemically, the benign fatty streak found in human arteries, rather than the raised fibrous plaque (Wissler, et al., in G. R. V. Born, Factors in Formation and Regression of the Atherosclerotic Plaque, Plenum Press, New York, pp. 59–78, 1972). In 1971, Kritchevsky and coworkers added various edible oils to a high cholesterol diet in rabbits, and reported that the diet containing 8% peanut oil plus 2% cholesterol caused aortic lesions which were more severe and of markedly elevated collagen content relative to those caused by cholesterol alone or with other oils (Kritchevsky, et al., Atherosclerosis 14; 53–67, 1971). This model of fibrous-fatty aortic atherosclerosis has since been used by many investigators as summarized by Camejo (Advances in Lipid Research 19; 1–53, 1982), and was used in the study of doxazosin described herein. Extrapolation to, and correlation of this procedure, with human utility is accepted by investigators in this field.

The study included 40 male normotensive New Zealand white rabbits, body weight 3 to 3.5 kg, randomly divided into five groups, eight animals per group. It followed the procedure of Kramsch, et al., J. Clin. Invest. 65, 967–981 (1980). The study lasted about 7.5 weeks, during which time animals in each group received diets and were administered drug as follows: Normal control (NC) rabbits were fed standard pelleted laboratory rabbit chow. All other rabbits in all groups were fed standard rabbit chow soaked with 10% by weight of a solution of cholesterol in peanut oil (1:4) (Krichevsky, et al., op. cit.). The selected drugs were prepared by dissolution in distilled water and sterilized by filtration. The normal control (NC) rabbits and the atherogenic control (AC) rabbits received a dose of 1 ml sterile filtered distilled water twice a day. Group I was dosed twice a day with 50 mg/kg b.i.d of trimazosin, Group II was dosed twice a day with 5 mg/kg b.i.d. of doxazosin and Group III was dosed twice a day with 2 mg/kg b.i.d. of prazosin. All dosages for the control groups and Groups I, II and III were administered via intraperitoneal injection. The above regimen was continued for about 7.5 weeks at which time a number of the rabbits from control and treated groups began to develop peritonitis, presumably from prolonged intraperitoneal dosing. Then, the rabbits were sacrificed, the aortas were excised in their entirety, rinsed and weighed. The contours of the aortas were examined, photographed and traced to determine the percent of the surface area involved with plaque, as described by Kramsch et al., op. cit. Samples were then removed for histological and enzymological study, standardized segments of aortas were prepared, the aortic intima-media was removed and assayed for content of the following constituents: dry weight (lypholized), collagen (tissue hydroxylproline), elastin, total cholesterol (free and ester), calcium and phosphorus.

The percent of total aortic area with visible plaque, as determined by computerized image analysis of photographs of aortas, and semi-subjective scoring (scale 0 to 3) of aortic plaque involvement is shown in Table I below for AC and Groups I and II rabbits.

TABLE I

AORTIC PLAQUE INVOLVEMENT

| Treatment Group | Image Analysis (% Involvement) | Visual Scoring (0 to 3 Scale) |
| --- | --- | --- |
| AC | 20.6 | 1.7 |
| Group I (Trimazosin) | 20.8 | 2.7 |
| Group II (Doxazosin) | 2.6 | 0.4 |

The data in Table I show that doxazosin significantly reduced the involvement of the aorta with atherosclerotic plaque. In contrast, no such reduction was found with trimazosin.

As shown in Table II below, the total cholesterol content (lipid deposition) in the aortic arch segment in comparison to the AC rabbits was increased by trimazosin (Group I) and unaffected by doxazosin (Group II). Prazosin (Group III) increased the total cholesterol content in the thoracic segment and had very little effect on the cholesterol content in the abdominal segment. However, doxazosin caused a marked reduction in total cholesterol in the distal (thoracic and abdominal) segments.

TABLE II

TOTAL CHOLESTEROL CONTENT OF SELECTED AORTIC SEGMENTS PER UNIT AREA

| Aortic Segment | Total Cholesterol (Ester and Free) ($\mu g/cm^2$) | | | | |
| --- | --- | --- | --- | --- | --- |
| | NC | AC | Group I (Trimazosin) | Group II (Doxazosin) | Group III (Prazosin) |
| Arch | 200 | 400 | 540 | 420 | NR* |
| Thoracic | 100 | 180 | 150 | 110 | 270 |
| Abdominal | 90 | 170 | 140 | 80 | 160 |

*NR = Not Reported

The dry weight per unit area, shown in Table III below, which is a measure of wall thickness, was increased by the atherogenic diet (AC). This thickening was prevented by both trimazosin (Group I) and doxazosin (Group II) but not by prazosin (Group III). The increased thickness of the aortic wall was accompanied by an increase in collagen per unit area.

TABLE III

DRY WEIGHT OF SELECTED AORTIC SEGMENTS PER UNIT AREA

| Aortic Segment | Dry Weight ($mg/cm^2$) | | | | |
| --- | --- | --- | --- | --- | --- |
| | NC | AC | Group I (Trimazosin) | Group II (Doxazosin) | Group III (Prazosin) |
| Arch | 10.9 | 13.6 | 11.6 | 11.9 | 14.6 |
| Thoracic | 7.6 | 8.3 | 7.5 | 6.8 | 8.1 |
| Abdominal | 8.3 | 8.7 | 7.5 | 7.1 | 7.8 |

It was noted that the elastin content of the aortic segments was little affected by any of the drugs.

Thus, administration of doxazosin to rabbits during development of fibrotic fatty aortic plaques caused an overall decrease in aortic atherosclerotic plaque involvement as well as a decrease in aortic cholesterol content (decreased lipid deposition) in distal aortic segments and no statistically significant increase in cholesterol content of the aortic arch segment. In contrast, prazosin administration resulted in an increase in total cholesterol content of the thoracic segment, with very little, if any, decrease in cholesterol content of the abdominal aortic segment. Trimazosin did not decrease aortic atherosclerotic plaque involvement and had very little, if any, effect on cholesterol content in the thoracic and abdominal segments. Doxazosin had a comparable effect to trimazosin on dry weight of the various aortic segments tested but was markedly better than prazosin, which increased the dry weight of the aortic arch segment and had little or no effect on the dry weight of the thoracic and abdominal segments.

I claim:

1. A method of suppressing fibrosis and lipid deposition of atherosclerotic lesions and of reducing atherosclerotic lesions in a mammal having atherosclerosis which comprises administering to said mammal an atherosclerotic lesion reducing and a fibrosis lesion and lipid deposition suppressing amount of doxazosin or a pharmaceutically acceptable acid addition salt thereof.

2. The method of claim 1 wherein doxazosin is administered.

3. The method of claim 1 wherein the doxazosin or a pharmaceutically acceptable acid addition salt thereof is administered orally.

4. The method of claim 1 wherein the doxazosin or a pharmaceutically acceptable acid addition salt thereof is administered intraperitoneally.

5. The method of claim 1 wherein the doxazosin or a pharmaceutically acceptable acid addition salt thereof is administered transdermally.

6. The method of claim 1 wherein the doxazosin or a pharmaceutically acceptable acid addition salt thereof is administered parenterally.

* * * * *

UNITED STATES PATENT AND TRADEMARK OFFICE
CERTIFICATE OF CORRECTION

PATENT NO. : 4,758,569
DATED     : July 19, 1988
INVENTOR(S) : Archie C. Swindell It is certified that error appears in the above-identified patent and that said Letters Patent is hereby corrected as shown below:

Column 2, lines 55-61, the Formula should read:

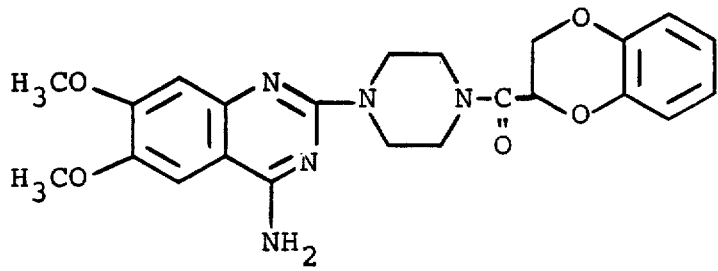

Signed and Sealed this

Sixth Day of December, 1988

*Attest:*

DONALD J. QUIGG

*Attesting Officer*        *Commissioner of Patents and Trademarks*